US011366916B1

(12) United States Patent
Caplovitz (10) Patent No.: US 11,366,916 B1
(45) Date of Patent: Jun. 21, 2022

(54) SYSTEMS AND METHODS FOR SECURING AND SHARING DATA USING DISTRIBUTED LEDGER TECHNOLOGY

(71) Applicant: GetChkd Inc., Dallas, TX (US)

(72) Inventor: Michael Caplovitz, Marietta, GA (US)

(73) Assignee: GETCHKD INC., Dallas, TX (US)

( * ) Notice: Subject to any disclaimer, the term of this patent is extended or adjusted under 35 U.S.C. 154(b) by 0 days.

(21) Appl. No.: 17/154,506

(22) Filed: Jan. 21, 2021

Related U.S. Application Data (60) Provisional application No. 62/964,069, filed on Jan. 21, 2020.

(51) Int. Cl.
| | |
|---|---|
| *G06F 21/62* | (2013.01) |
| *G16H 10/60* | (2018.01) |
| *H04L 9/30* | (2006.01) |
| *G06Q 20/36* | (2012.01) |
| *H04L 9/06* | (2006.01) |
| *H04L 9/40* | (2022.01) |

(52) U.S. Cl.
CPC ...... *G06F 21/6209* (2013.01); *G06F 21/6245* (2013.01); *G06Q 20/36* (2013.01); *G16H 10/60* (2018.01); *H04L 9/0643* (2013.01); *H04L 9/30* (2013.01); *H04L 63/0407* (2013.01); *H04L 63/0428* (2013.01); *H04L 2209/38* (2013.01)

(58) Field of Classification Search
CPC .......................... G06Q 50/22–24; G06Q 20/36
See application file for complete search history.

(56) References Cited

U.S. PATENT DOCUMENTS

| | | | |
|---|---|---|---|
| 2019/0354693 A1* | 11/2019 | Yoon | G06F 21/6245 |
| 2019/0358515 A1 | 11/2019 | Tran et al. | |
| 2020/0211409 A1* | 7/2020 | Latorre | G16H 20/30 |

(Continued)

FOREIGN PATENT DOCUMENTS

| | | | | |
|---|---|---|---|---|
| CA | 3033385 A1 * | 8/2016 | | G16H 10/60 |

OTHER PUBLICATIONS

Girase, R. (2018). Personal data vault management system and secured data access to service provider using blockchain technology (Order No. 10836925). Available from ProQuest Dissertations and Theses Professional. (2050554654). (Year: 2018).*

(Continued)

*Primary Examiner* — Jason S Tiedeman
*Assistant Examiner* — Emily Huynh
(74) *Attorney, Agent, or Firm* — Norton Rose Fulbright US LLP (57) ABSTRACT

Embodiments of the present disclosure disclose a distributed ledger technology (e.g., blockchain)-based system that provides tools and mechanisms to place users in control of their data. In embodiments, the system may include a platform device configured to initiate a connection with a lab test service provider whose systems (e.g., computer systems) may store data pertaining to the user. In embodiments, the platform device is configured to secure the data stored at the lab test service provider by facilitating deployment of that data into a distributed ledger. Once the data is secured in the distributed ledger, the platform device may be configured to provide controlled distribution or sharing of the secured data with other users or other third-party systems.

18 Claims, 3 Drawing Sheets

(56) References Cited

U.S. PATENT DOCUMENTS

2020/0226285 A1* 7/2020 Bulleit .................... G06F 21/33
2020/0334379 A1* 10/2020 DeRosa-Grund ..... H04L 9/3255

OTHER PUBLICATIONS

Patent Cooperation Treaty, International Search Report and Written Opinion issued for PCT Application No. PCT/IB2021/050469, dated May 25, 2021, 8 pages.

* cited by examiner

SYSTEMS AND METHODS FOR SECURING AND SHARING DATA USING DISTRIBUTED LEDGER TECHNOLOGY

CROSS-REFERENCE TO RELATED APPLICATION

The present application claims priority from U.S. Provisional Patent Application No. 62/964,069 filed Jan. 21, 2020 and entitled "SYSTEMS AND METHODS FOR ACCESSING, SECURING, AND SHARING DATA USING A BLOCKCHAIN ENVIRONMENT," the disclosure of which is incorporated by reference herein in its entirety.

TECHNICAL FIELD

The present application relates to systems and methods for enabling users to secure and share data pertaining to them using distributed ledger technology. The systems and methods disclosed herein thus enable the users to control ownership of data pertaining to them.

BACKGROUND

Sexually transmitted diseases and infections—collectively herein referred to as sexually transmitted diseases (STDs)—are considered to be a silent epidemic. Millions of new cases are detected and reported every year. Currently used electronic dating solutions, including websites and mobile applications are fueling the growth of STD rates because of certain high-risk behaviors, including using these dating sites to arrange casual and often anonymous sexual encounters. Sometimes people with STDs engage in sexual encounters without revealing their disease or sometimes people just think or hope that their partner does not have an STD. In some cases, people who have an STD do not show the symptoms associated to the STD because many STDs show no signs or symptoms (and thus are asymptomatic). Even with no symptoms, however, people can pass the infection to their partners. As such, people who engage in sexual encounters can knowingly or unknowingly pass their disease on to some or all of their partners. This makes STDs common and often invisible.

Some electronic dating solutions provide their users an option to reveal details about their STD status. For example, some dating websites provide users the ability to disclose whether they have an STD and/or disclose the type of STD they possess. However, such electronic dating solutions often lack details and/or proof related to when the users got their STD-related lab tests done. This information is important as the user may have knowingly or unknowingly acquired a different or multiple STDs. Furthermore, the current solutions rely heavily on users to voluntarily discuss or truthfully share information pertaining to their STDs. Thus, existing electronic dating solutions do not provide important or reliable details related to other users' STD status for them to make an informed decision when meeting new people with whom they may have a sexual encounter. This could be because these solutions also do not provide systems that allow users to securely control (e.g., access, secure, or share) their verified (e.g., by a lab) STD data (or a part of their STD data) which then allows the users to make the informed decision.

The issue of a disease spreading amongst the human population is not limited to STDs. Coronavirus disease 2019 (COVID-19) is another disease which has been silently spreading throughout the world and hundreds of thousands of new cases are detected and reported every day. Human behavior (e.g., desire to have social contact or perform recreational activities) and need for survival (e.g., going to work or shopping at a grocery store) can be considered as some of the reasons that are fermenting COVID-19 spread. Organizations and/or governments have implemented social distancing restrictions to control (e.g., reduce) the spread. These social distancing efforts have led to remote working; remote or online education; cancellation of sporting, entertainment, and professional events; restricted entry in grocery stores; and, closures of museums, parks, churches and much more.

Going forward, organizations are likely to implement systems that help them reopen their facilities and operate at pre-COVID levels. In order to do that, organizations may need to determine COVID-19 status of the users entering their facilities to determine whether to allow them to enter their premises. For example, organizations may need to determine whether someone entering their facilities is COVID-19 positive/negative or have received a vaccine to make that determination. To illustrate, an organization, such as a meat plant owner whose business does not allow one or more users (e.g., employees, purchaser, distributors, and the like) associated with them to attend to their business (e.g., perform meat cutting) from home, may implement a system that helps them make an informed decision about whether to allow one or more users to enter their facility. To further illustrate, another organization, such as a concert operator or live entertainment provider whose business also does not allow attendees to perform the recreational activity from home may also implement such a system in order to make an informed decision about whether to allow an attendee to enter their premises.

To make the above-noted determination, as a temporary solution, an organization may require users to submit a 1) questionnaire detailing their current health conditions (e.g., whether they have experienced one or more of the COVID-19 symptoms), and/or 2) a current (e.g., recently tested) COVID-19 status. However, implementing these testing and other health monitoring efforts results in the collection of massive amounts of personal data, and questions can be raised—by the users or government authorities—regarding the integrity of the security of the users' personal data. This brings about additional liability concerns on the part of the organization as it would require them to disclose at least to the users the data that is being protected, how it's being protected, from whom it's being protected, and who is responsible for that protection. Thus, the existing solutions with respect to implementing health monitoring efforts to reopen organizations do not provide systems that allow users to securely control (e.g., access, secure, or share) their personal data (e.g., health data) with one or more organizations, which further impedes organizations to implement their health monitoring efforts.

SUMMARY

Embodiments of the present disclosure address these challenges and disclose a distributed ledger technology (e.g. blockchain)-based system that provides tools and mechanisms to place users in control of their data. Providing users the control of their data may enable them to securely share data pertaining to them (e.g., health data such as STD status, COVID status, and the like) with third parties, such as another user or entity/organization and help the another user/organization make an informed decision. To illustrate, the systems and methods provide users the ability to gather information about themselves (e.g., their health data such as STD or COVID status) from a third-party system (e.g., lab test service provider's system), secure that data using distributed ledger technology, and share the data with another third-party system (e.g., in a dating environment or to an organization determining whether to allow the user to enter their facility in light of the COVID pandemic) using customizable permissions. When used in a dating-based application, being able to securely share up to date STD status-related data provides users transparency and the ability to make an informed decision when choosing whom they wish to engage, speak, message, or meet and whether they want to engage in sexual activity. And when used in a pandemic-related (e.g., COVID-19) application, being able to securely share up to date COVID status-related data (e.g., user's COVID-19 test results, or COVID-19 vaccination-related details) third parties to make an informed decision regarding whether to allow a user in their facility.

In embodiments, the system may include a platform device configured to initiate a connection with a lab test service provider whose systems (e.g., computer systems) may store data pertaining to the user. In embodiments, the platform device is configured to secure the data stored at the lab test service provider by facilitating deployment of that data into a distributed ledger. Once the data is secured in the distributed ledger, the platform device may be configured to provide controlled distribution or sharing of the secured data with other users or other third-party systems. In embodiments, the system may include a platform device which may include a user interface running on a computer system that enables users to create a platform profile by verifying themselves. As is described in detail below, once a user verifies themselves, the platform device may issue a set of keys (e.g., private key and a corresponding public key) to the user (or the user's verified profile) and store the user's public key and/or public key address (e.g., hashed copy of the public key) in a local storage associated with the platform. After having public/private keys provided or issued to their verified profile, the user may access the services provided by the platform. In aspects, the services may include enabling the user to initiate a connection with a third-party system (such as a lab test service provider) who may have data pertaining to the user stored in their computer system. In embodiments, the services may further include facilitating deployment or storage of the data stored in the third-party system into a distributed ledger. For example, after performing the lab test and once the lab test results are available, the platform device may be configured to facilitate the deployment (or storage) of the data (e.g., lab test results) stored in the lab test service provider's system into a distributed ledger (or a blockchain network). After storing the data from the third-party system, in embodiments, the services provided by the platform device may also include providing the user the ability to control (e.g., using permissions or smart contracts) the distribution or sharing of the data (e.g., lab test results) stored in the distributed ledger with other users or other third-party systems.

In embodiments, the platform device may also be configured to receive other information pertaining to the user and deploy it onto the blockchain. For example, the platform may be configured to receive personal information from the user, such as name, contact information, social media information, identity verification information, background information, or any other details provided to the platform device by the user, and deploy an encrypted version of this data into a distributed ledger. The data, before being stored into the distributed ledger, may be encrypted (e.g., using the public key issued to the user). For example, the platform device may be configured to receive personal information pertaining to a user, encrypt this data using the user's public key, and then deploy the encrypted data to a distributed ledger. In embodiments, the user data sourced from the third-party system, before being stored into the distributed ledger, may also be encrypted, for example, by the encryption provided by the blockchain network. As such, in aspects, the data encrypted using public key can be decrypted only by the private key which is stored in a digital wallet (or a key manager) in the user's personal device. Furthermore, in aspects, the data gathered from the third-party system and encrypted by the blockchain network can also only be decrypted and accessed by the user (e.g., upon accessing or sharing), thereby giving the user complete ownership of the data stored in the distributed ledger, without the platform device storing any of the decryption keys in their local storage. In that sense, the platform can never decrypt and therefore access any information pertaining to the user from the blockchain, and thereby giving data ownership to the user.

In embodiments, the user, using the platform device, can control (e.g., limit) the amount of information that is to be shared with a third-party (e.g., dating platform or another user or an organization). In aspects, the user may be able to control (e.g., limit) the information that may be available to the third-party (or, in essence, anywhere on the internet) by using a set of permissions and/or smart contracts, thus gaining complete control on the distribution of their personal information and how it is shared. In aspects, the user devices may maintain a digital wallet (or a key manager) which stores the public and private keys (and all other decryption keys) associated with the user's data stored in the blockchain ledger.

In embodiments, particularly in embodiments configured to comply with regional data security laws, the platform may be configured to store an encrypted version of the personal identifiable information (PII) pertaining to the user in an off-chain storage (e.g., in a personal data collection of the hyper ledger fabric). The platform may further be configured to store the user's public key and/or public key address into the off-chain storage. The platform may also be configured to store a hash of the user's PII into the off-chain storage. In aspects, the platform may be configured to retrieve and/or identify the information stored in the off-chain storage using the user's public key (or public key address) or the hash of the PII or any token that can retrieve encrypted versions of the user's PII. The platform, in such embodiments, may be configured to facilitate storing the non-personally identifiable information (non-PII) pertaining to the user (e.g., STD status, COVID status, temperature info, answers to questionnaires, etc.) to the distributed ledger. In aspects, the non-PII may be encrypted by the blockchain network such that only the encrypted version of the non-PII is stored on the blockchain. In aspects, the user, using the platform device, can view the deployed data using an application (e.g., web application) and share their non-PII (e.g., whether the user has an STD, or whether the user tested positive or negative for COVID) with one or more third parties by using a set of permissions and/or smart contracts.

The foregoing broadly outlines the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

For a more complete understanding of the present invention, reference is now made to the following descriptions taken in conjunction with the accompanying drawings, in which.

DETAILED DESCRIPTION

Various features and advantageous details are explained more fully with reference to the non-limiting embodiments that are illustrated in the accompanying drawings and detailed in the following description. Descriptions of well-known processing techniques, components, and equipment are omitted so as not to unnecessarily obscure the invention in detail. It should be understood, however, that the detailed description and the specific examples, while indicating embodiments of the invention, are given by way of illustration only, and not by way of limitation. Various substitutions, modifications, additions, and/or rearrangements within the spirit and/or scope of the underlying inventive concept will become apparent to those skilled in the art from this disclosure.

The system described ahead includes a platform device that may enable gathering user data stored in a third-party system (e.g., lab test results stored at the lab service provider site) and facilitate deployment of the user data stored on the third-party system to a distributed ledger. Such deployment may occur without having ever stored the data on the platform device. The platform device further may enable controlled distribution or sharing of the user data stored on the distributed ledger at least partially or entirely based on a user's discretion at various points in time. In this sense, aspects of the present disclosure provide for a mechanism for securing and sharing personal data. Systems implemented in accordance with aspects of the present disclosure may be considered blockchain as a service (BAAS) systems or software that uses blockchain protocol and thus can be viewed as deployed on a blockchain.

The disclosure that follows focuses on an application related to health/medical data (e.g., STD or COVID-19 test and/or vaccination status). In particular, some of the disclosure focuses on 1) gathering user data by enabling the users to initiate a connection with a lab test service provider whose systems (e.g., computer systems) may store data pertaining to the user, 2) facilitating deployment of the data stored in the lab test provider's system into a distributed ledger. In that sense, the disclosure that follows provides user the ability to secure user data stored in a third-party system (e.g., lab test provider's system) to a distributed ledger and the ability to access the data using an application (e.g., web application or a dashboard). Some of the disclosure also focuses on 3) providing controlled distribution or sharing of the secured data with other users or other third-party systems. In that sense, the disclosure that follows provides user the ability to share the data now secured in the distributed ledger to other users or systems. It will be appreciated that the disclosure herein is equally applicable to gathering any kind of user data (i.e., not just lab test data) stored in any third-party system; securing the data from the third-party system into a distributed ledger; and sharing the secured data with any user or system or service provider.

Figure 1:
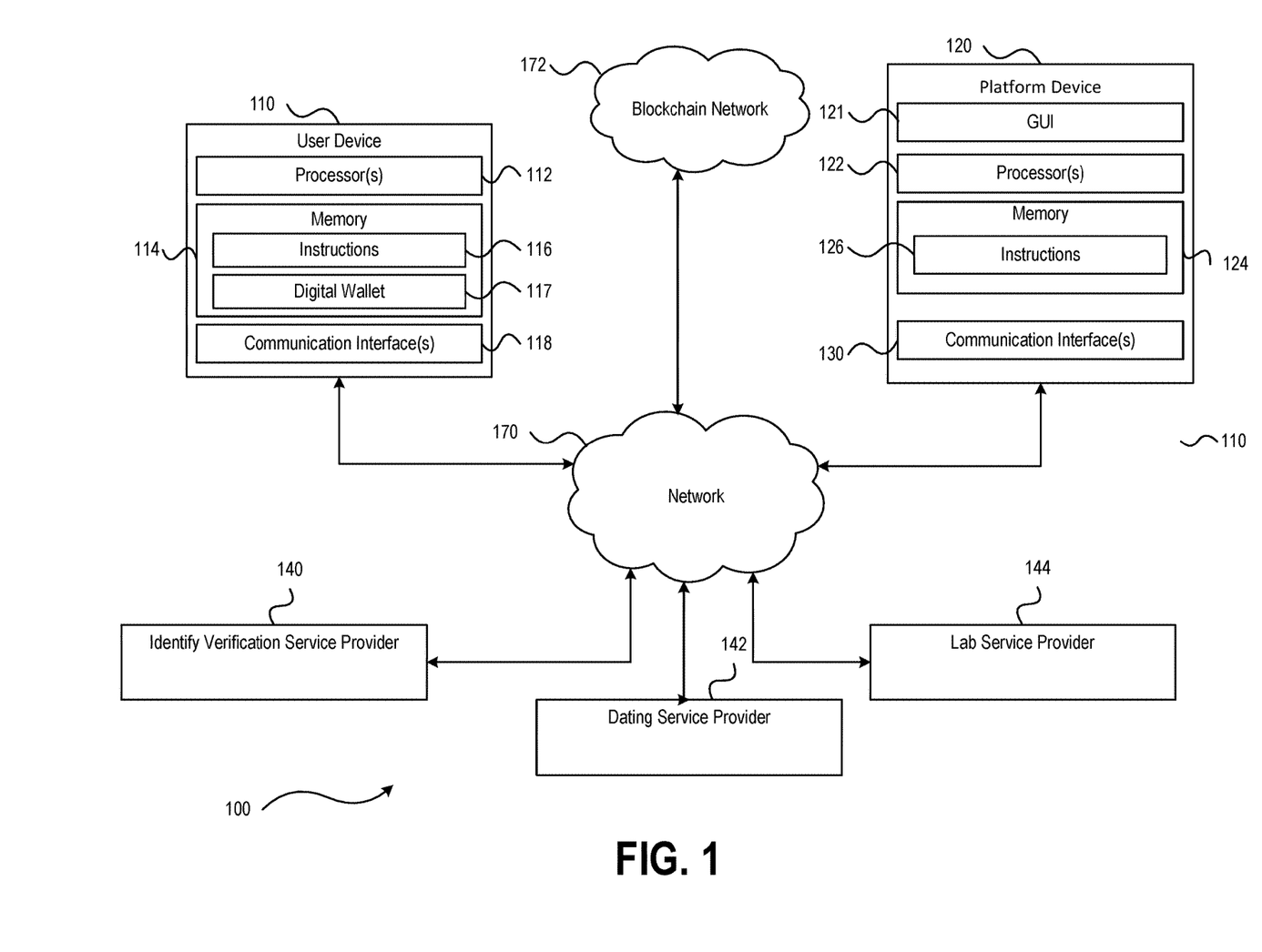
FIG. 1 shows a system configured to perform operations in accordance with embodiments of the present disclosure.

FIG. 1 is a block diagram of a system 100 including a platform device 120 which provides users the ability to secure user data using distributed ledger technology and control the distribution of the secured data, according to embodiments of the present disclosure. System 100 includes platform device 120, one or more user devices 110, and multiple service providers, such as identity verification service provider 140, dating service provider 142, and lab service provider 144. According to embodiments of the present disclosure, the platform device 120 is configured to secure lab test data stored with a lab service provider (e.g., at the lab service provider computer system) using distributed ledger technology and share the secured data (or a part thereof) to another one of the service providers (e.g., dating service provider).

It is noted that while FIG. 1 shows service providers related to medical/health service and dating service, it is to be understood that systems in accordance with the present disclosure may include different service providers based on the application in which the system 100 is employed. For example, in other applications, instead of securing user data from a lab service provider, the system 100 may secure data from social media service provider (e.g., Facebook). In such application, the third-party with whom the secured data is shared could be any third-party (e.g., video streaming service provider or another user or any other internet enabled computer system). It is to be further understood that systems in accordance with the present disclosure may include additional or fewer service providers based on the application in which the system 100 is employed. For example, the system 100 may include identity verification service provider 140, a lab service provider, and a social media service provider, and the system may secure data from both the lab service provider and social media service provider. In such application, the third-party with whom the secured data is shared could be any third-party system (e.g., computer systems of a hotel service provider, travel company, and/or government institutions).

As illustrated in FIG. 1, platform device 120, one or more user devices 110, and the multiple service providers may be communicatively coupled to one or more networks 170 via one or more wired or wireless communication links. The one or more networks 170 may include a wired network, a wireless communication network, a cellular network, a cable transmission system, a Local Area Network (LAN), a Wireless LAN (WLAN), a Metropolitan Area Network (MAN), a Wide Area Network (WAN), the Internet, the Public Switched Telephone Network (PSTN), cellular data networks, cellular voice networks, the Internet, and the like. The platform device 120, one or more user devices 110, and the multiple service providers may also communicatively couple to a blockchain network 172. The blockchain network 172 may implement the blockchain technology and execute functionalities provided by blockchain platforms such as Ethereum, Hyperledger Fabric, IBM Blockchain, Multichain, and/or any other blockchain platform. It is noted that, the systems implemented in accordance with aspects of the present disclosure may be blockchain-platform agnostic, and any discussion of a particular blockchain example is made for illustrative purposes, and should not be construed as limiting.

The user device 110 includes one or more processors 112, a memory 114, and one or more communication interfaces 118. Each of the one or more processors 112 may be a central processing unit (CPU) or other computing circuitry (e.g., a microcontroller, one or more application specific integrated circuits (ASICs), and the like) and may have one or more processing cores. The memory 114 may include read only memory (ROM) devices, random access memory (RAM) devices, one or more hard disk drives (HDDs), flash memory devices, solid state drives (SSDs), other devices configured to store data in a persistent or non-persistent state, or a combination of different memory devices. The memory 114 may store instructions 116 that, when executed by the one or more processors 112, cause the one or more processors 112 to perform the operations described in connection with the user device 110 with reference to FIGS. 1-3. In addition to storing the instructions 116, the memory 114 may also store a digital wallet 117. The digital wallet 117 may be configured to store information associated with a user corresponding to the user device 110, such as all data the user has stored on the distributed ledger. The digital wallet 117 may connect to or be included in an application (e.g., web application) provided by an entity that operates the platform device. The application may provide the user the control to share their data stored in the distributed ledger with other users or systems, for example, by changing (or customizing) the permissions to share the data from the distributed ledger. The application may be configured to provide the user a snapshot of the data the user has stored on the distributed ledger. The application may be configured to provide the user a snapshot of the data that the platform has secured—from third party systems (e.g., lab test service provider)—onto the distributed ledger.

User device 110 may be configured to provide an interface to facilitate user input and output operations in accordance with aspects of the present disclosure. The interface may include a graphical user interface (GUI). In embodiments, the GUI may be configured and generated by GUI system (e.g., GUI 121) of platform device 120. In other embodiments, the GUI may be configured and generated by GUI system (not shown in FIG. 1) of user device 110. GUIs, in either case, may be configured to configure and generate a GUI for facilitating input and output operations from/to a user. The GUI may be configured to include various GUI controls for allowing the user to input information, such as driver's license information, passport information, or any other eligible identification proof-related information, personal details (e.g., name, and contact information, or outputting information to the user, such as information related to their lab tests (e.g., STD or COVID-19 test and/or vaccination status). In aspects, the information attained from third parties (e.g., third-party dating platforms or services) may also be available via GUI. In essence, any information related to securing, accessing, and sharing lab test information and lab results can be managed and controlled by the user using the GUI. In some embodiments, the GUI may also include GUI controls for controlling various aspects of the process. For example, GUI controls may be provided for logging into the system, enabling the verification process, enabling initiating a connection with a third-party system (e.g., lab test service provider system), accessing data gathered from the third-party system and stored in the distributed ledger, authorizing sharing of data, etc. In embodiments, a user may use the GUI to input or share information about themselves, including verification information.

In aspects, user device 110 may be implemented as a mobile device, a smartphone, a tablet computing device, a personal computing device, a laptop computing device, a desktop computing device, a wearable computing device, a computer system of a vehicle, a personal digital assistant (PDA), a smart watch, another type of wired and/or wireless computing device, or any part thereof.

In aspects, the user device 110 may include an application provided by an entity that operates the platform device 120 and the application may be configured to present a GUI to the user that allows the user to view and use the services offered. The application may further be configured to provide access to smart contracts (or customizable permissions), which may be used by users to change the currently issued smart contract and/or permissions that controls the distribution of the data associated with the user stored on the distributed ledger. The application may further be configured to, via smart contracts, revoke permissions from third parties to prevent those third parties to view one or more previously visible information about the user. The application may yet further be configured to connect to or include the digital wallet (or key manager) that stores the keys associated with the user, such as the private key of the user. In embodiments, the application employs the keys stored in the digital wallet to decrypt data and present decrypted versions of the data (e.g., data pertaining to user stored on the distributed ledger) to the user. The application may be a mobile application, a browser-based application (e.g., an application accessible over the Internet via a Web browser), or other type of application running on a smartphone, a tablet computing device, a desktop or laptop computing device, a personal digital assistant, or other type of electronic device adapted to perform the operations of the user device 110.

The platform device 120 may include GUI 121, one or more processors 122, a memory 124, and one or more communication interfaces 130. Each of the one or more processors 122 may be a CPU or other computing circuitry (e.g., a microcontroller, one or more ASICs, and the like) and may have one or more processing cores. The memory 114 may include ROM devices, RAM devices, one or more HDDs, flash memory devices, solid state drives SSDs, other devices configured to store data in a persistent or non-persistent state, or a combination of different memory devices. The memory 124 may store instructions 126 that, when executed by the one or more processors 122, cause the one or more processors 122 to perform the operations described in connection with the platform device 120 with reference to FIGS. 1-3.

Although FIG. 1 shows a single platform device 120, it will be appreciated that platform device 120 and its individual functional blocks may be implemented as a single device or may be distributed over multiple devices having their own processing resources, whose aggregate functionality may be configured to perform operations in accordance with the present disclosure. In some embodiments, platform device 120 may be implemented, wholly or in part, on an on-site system, or on a cloud-based system.

Figure 2:
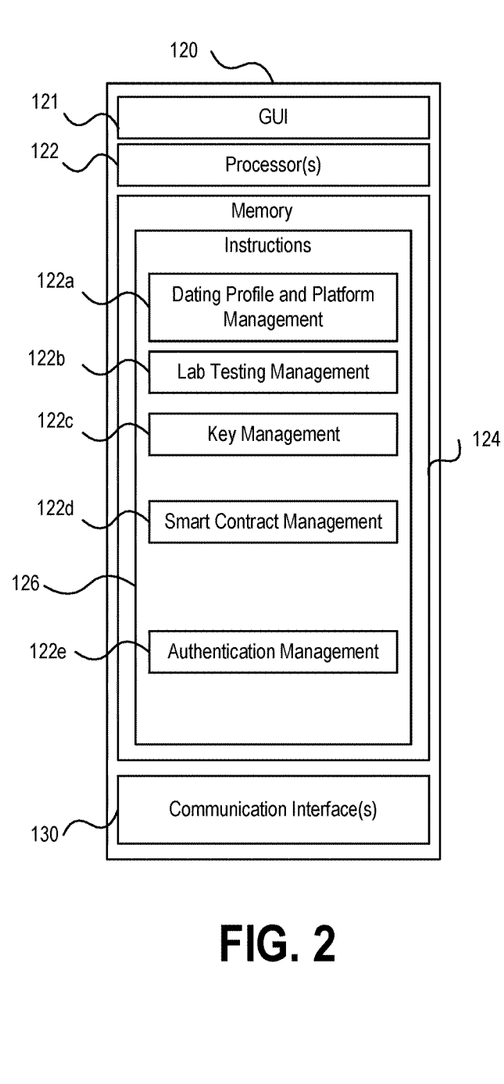
FIG. 2 shows the platform device of FIG. 1 in accordance with embodiments of the present disclosure.

Briefly referring to FIG. 2, which shows the platform device 120 in greater detail. The instructions 126 may include instructions related to verification management 122e, key management 122c, and smart contract management 122d. The embodiments in which the system securely gathers data from a lab service provider, the instructions 126 may further include lab testing management 122b and dating profile and platform management 122a. The platform device 120 may further include a GUI system 121. In embodiments, each of the instruction instances (e.g., 122a-122e) may have one or more application programming interfaces (APIs) associated with them. For example, each of the dating profile and platform management 122a, lab testing management 122b, key management 122c, smart contract management 122d, and verification management 122e may have one or more APIs associated with them. It is noted that in some embodiments, APIs may not be distributed amongst the several instruction instances, and one or more APIs may perform functionalities of the instruction instances noted above. Referring back to FIG. 1, the one or more communication interfaces 130 may be configured to communicatively couple the platform device 120 to one or more networks 170 and blockchain network 172 via wired or wireless communication links according to one or more communication protocols or standards (e.g., the one or more communication standards described above with reference to the one or more networks 170).

Further illustrated in FIG. 1 are multiple service providers, namely identity verification service provider, third-party service provider, and lab service provider. These service providers provide different services to the user via the platform device 120. For example, the identity verification service provider provides identity verification services to the platform device. Similarly, lab service provider 144 may provide lab testing services to the user with the help of the platform device 120. Dating service provider 142 may provide secure dating services to the user via the platform device 120. Each of the multiple service providers may be operable on their own computer systems, each including its own processor, memory, and one or more communication interfaces. In embodiments, the instructions stored in the memory 124 of the platform device 120 may facilitate the interaction of the platform device 120 with one or more of the multiple service providers.

The functionalities provided by each of these instruction instances are now described. The platform device 120 may call on instructions related to verification management 122e when a user attempts to register to access the services provided by the platform device 120. In embodiments, verification management 122e may provide functionalities including activating a GUI control (e.g., in user device 110) that allows the user to submit personal details, for example, name, contact information, state identification information (e.g., driver's license number, passport number). In aspects, the verification management 122e may also activate a GUI control that request the user to scan and/or share pictures of their state identification or passport along with other government issued identification proofs. The information input by the user may directly be sent via one or more networks 170 to identity verification service provider 140 (e.g., ACUANT®) and without storing any information in the memory 124. For example, the API corresponding to the verification management 122e may be used to communicate the information submitted by the user to the identity verification technology service provider. In embodiments, during or after submitting the information to the service provider, the verification management 122e may notify the key management 122c to generate a unique ID corresponding to the verification request.

In embodiments, the verification management 122e, when a user attempts to register to access the services provided by the platform device 120, may provide functionalities including activating a GUI control (e.g., in user device 110) that provides a link (e.g., web site link) to the verification service provider 140. When the user indicates interest to verify themselves, for instance by clicking to the link to the verification service provider, the verification management 122e may direct the user to the verification service provider 140 and indicate to key management 122c (as further described below) the user's interest to get verified. The key management 122c may then generate a unique ID corresponding to the indication. In the latter scenario, the user provides identity verification information directly to the verification provider system, bypassing the need to provide identity verification information to the platform device 120.

Once the verification is complete, the results may be sent back via API to platform device 120 and associated with the user using the unique ID. The results may then be provided to the user. The results may include information that the user is successfully verified, i.e., the identity verification service provider has successfully verified the user's real world identity online and that the service provider believes, based on the information and/or documents provided by the user, that the user is who he or she says they are. Upon successful verification, the verification management 122e may provide functionalities including notifying the platform device 120 of the successful verification (e.g., by transmitting an internal notification), which may prompt the platform device 120, using the key management system 122c to generate a profile or platform ID for the user. In aspects, the platform device 120 may also be prompted to, using the smart contract management 122d or the key management system 122c, provide a digital wallet (e.g., a key manager) to the user. In aspects, the platform device 120 associates the platform ID to the digital wallet.

To further illustrate, the platform device 120 may call on instructions (and execute based on the instructions) related to key management 122c when a user is successfully verified by the identify verification service provider. Key management 122c, in that case, may generate a platform ID (e.g., an identification of the user internal to platform device 120) to the user and a public key and a corresponding private key to the verified user. Key management 122c may store a copy of the public key issued to the user in memory 124, but it does not stores the private key provided to a user in memory 124. In embodiments, the key management 122c may associate the platform ID to the user's public key and store that association information in platform device 120. In embodiments, once provided, the user may store their private key generated for them in the digital wallet 117 or in a cold storage wallet (e.g., somewhere offline, such as in a memory stick or on a private diary).

In aspects, the key management system 122c may provide the keys to the user using a key management system such as AMAZON WEB SERVICE® (AWS) Key Management Service, Bell ID® Key Manager, IBM® Security Key manager, and the like. Key management 122c may further provide functionality related to exchange, crypto-shredding (destruction of keys) and replacement of keys. Key management 122c may include cryptographic protocol design, key servers, user procedures, and other relevant protocols. Key management 122c may be configured to provide keys at the user level, either between users or systems (e.g., third-party systems such as dating service provider, lab service provider 144).

In embodiments, key management 122c may be configured to provide keys such as tokens or unique IDs at the user level, either between users or systems. For instance, when a user indicates interest to verify themselves or schedule an STD or COVID-related test from a lab service provider, the key management 122c may generate a unique ID corresponding to the request and associate the unique ID with the copy of the public key of the user. In embodiments, the key management 122c may associate the unique ID with the public key address (which is a hash of the public key of the user). In embodiments, the key management 122c may associate the unique ID with an asset ID of the user; the asset ID may be generated by the key management 122c upon successful verification of the user. The asset ID may be associated with the digital wallet of the user. In aspects, the data stored in the distributed ledger may be associated with the user using asset ID of the user. In aspects, key management 122c generates a set of keys (e.g., another set of asymmetric keys such as public and private keys) when user sends personal details to the lab service provider 144. In aspects, key management 122c generates a different set of keys (e.g., another set of asymmetric keys such as public and private keys) when user sends personal details to the dating service provider 142.

Furthermore, the platform device 120 may call on instructions related to lab testing management 122b when a user is successfully verified and indicates interest to schedule a lab test (e.g., STD or COVID-related test) from a lab service provider. For example, once the user is verified and is provided a set of keys, the lab testing management 122b may conjure the GUI system to provide to the user the ability to request lab tests, such as by providing a link (e.g., website link) to the lab service provider 144. When the user indicates interest to schedule a lab test, for instance by clicking to the link, the lab testing management 122b may direct the user to a website corresponding to the lab service provider 144 and notify to key management 122c the user's interest to schedule a lab test. As noted above, when a user indicates interest to schedule a lab test from a lab service provider, the key management 122c may generate a unique ID corresponding to the lab test request, transmit, via API of the lab testing management 122b, the unique ID to the lab service provider (or system thereof), and associate the unique ID with the user in the platform device 120 (e.g., using platform ID or public key of the user). In embodiments, the association between the unique ID and the user may be stored in memory 124. As noted above, the unique ID is transmitted to the lab test provider and is associated with the user internally, and at least in that sense, the platform device 120 initiates a connection with the lab test provider.

Upon completion of the lab test (e.g., after the user has submitted the sample and the lab has the result), the lab testing management 122b may receive a notification, such as in the form of an API call from the API of the lab service provider 144. For example, when the lab testing management 122c receives the notification from lab service provider 144, the lab testing management 122c, along with the key management 122c may direct the lab results to be stored in the distributed ledger. The direction from the key management 122c may include providing, in return to the API call, the association information between the unique ID and the user, which facilitates the storage of the results in the distributed ledger. In that sense, the test results are never stored locally in memory 124. The user may then securely access (e.g., view) the results using the application provided by platform device 120 and/or their digital wallet 117 (e.g., by providing decryption using the keys stored therein). In embodiments, the lab test results are encrypted before being stored in the distributed ledger. This encryption may occur at the blockchain network 172 (e.g., in the case of hyperledger fabric). In embodiments, the decryption of the lab test results may be performed by the blockchain network 172 without providing any decryption keys associated with the encryption.

Furthermore, the platform device 120 may call on instructions related to smart contract management 122d when a user has received the test results from a lab service provider 144. Smart contract management 122d may provide functionality related sharing the received lab test and/or any other data (e.g., dating bio, name, pictures, social media handles, etc.) stored in the distributed ledger that is accessible to the user. The sharing can be done with other users (e.g., any user on the dating service provider 142) using the application provided by the platform device 120. In other words, the user may use the application provided by the platform device 120 to control the sharing of the data pertaining to the user stored in the distributed ledger. Smart contract management 122d may include criterions that users need to select before sharing their data with other users. These criterions may include the amount of data that is being shared. For example, a user, using smart contracts, may only choose to send a portion of their test result (e.g., just their STD status related to a specific disease (e.g., herpes I) instead of the complete test result including status related to other diseases). As another example and as is further described below, the user may choose to share their complete profile, including name and contact information (for example in an application in which the sharing is done in a dating platform where users are deciding whether to sexually engage with someone), and complete STD profile (including the date the test was performed). The type of data shared can include data that is derived from the information stored in the distributed ledger. For example, if a user does not want to explicitly inform the other users on the dating service provider about the STDs the user has, a user, may only choose to put a badge on their third-party dating profile. The badge may signify that the user had taken an STD test, or that the user had received their STD test results and the user is either free from all tested STDs or user tested positive for at least one of the STDs. The badges may assume different color or shape depending upon the user's STD status. For example, a green badge or a green "check" sign may signify that the user has taken a test and is free from all the STDs. In other examples, the badge may assume a yellow "check" sign which may signify that the user has taken a test and has at least one STD. In other examples, the badge may assume a red "cross" sign, signifying that the user has not taken the test.

As noted above, the user may share derived information with other users or systems. In embodiments, the smart contracts may be utilized by platforms of the present disclosure to 1) derive results from user data stored in the distributed ledger and 2) provide user the ability to share the derived result. For example, smart contracts may be utilized to apply one or more protocols (or rules) to the user data stored in the distributed ledger to provide user the derived result and the ability to share the result with other users or systems. To illustrate, user data stored in distributed ledger may include the user's age, their COVID test results, vaccination-related information (e.g., whether they have received a vaccine, date of vaccination, proof of vaccination, etc.) and their STD results. The smart contracts may be configured or designed to apply a protocol that derives a "green" badge which may signify that the user has no STDs, is COVID negative, and is above a certain threshold age. The smart contracts may also provide user the ability to share that badge to other users or system, thereby preventing the need to share the data stored in the distributed ledger. In embodiments, smart contracts may provide permissions to other users to view user data on the distributed ledger but not share (e.g., make a copy) that data. The user may also revoke granted permissions.

Dating profile and platform management 122a may be configured to provide functionality to create dating profiles for a user, or in general, create a dating environment which could be accessed by the users using the GUI. The dating profile and platform management 122a may include providing a user an interface—configured by the GUI system 121 showing their own dating profile and dating profile of other users. In aspects, once the user has been verified, the dating profile and platform management 122a may suggest to the user to create their dating profile. To create the dating profile, the dating profile and platform management 122a may allow the user to add a bio, one or more pictures, information pertaining to their sexuality, and other dating related details. The information provided by the user in their dating profile may be encrypted and stored on the distributed ledger (e.g., a transaction record with the dating profile information may be stored on the distributed ledger). In aspects, since all the information pertaining to the user is deployed onto the blockchain, the user may choose to reveal whatever information they want to share. For example, dating profile and platform management 122a may be configured to provide functionality to users share their personal data, on their discretion (e.g., using smart contracts), to other dating platforms (or dating service provider). Examples of third-party dating platform include Bumble, Tinder, Shaadi.com, Match.com, etc. In aspects, the user may choose to keep some of information provided in the dating profile hidden from the other users by using smart contracts, as is described above with respect to smart contract management 122d.

In operation, the platform device 120, one or more user devices 110, and the multiple service providers and their individual components, may cooperatively operate to provide functionality in accordance with the discussion herein. In some aspects, the functionalities provided by system 100 may be provided, at least in part, as a web-based program, as a stand-alone application (e.g., mobile, and/or desktop-based), as a cloud-based application, as an application programming interface (API), etc. For example, user device 110 may be used by a user to provide information about themselves. The information may be communicated, via one or more networks 170, to platform device 120. Platform device 120 may include functionality to allow the user, via the user device 110, to get verified, then initiate a connection with the lab test service provider, facilitate storing the information pertaining to their health monitoring test results following the lab test into a blockchain network 172, and share their health monitoring test results (e.g., STD test date and status) with others. Further, as noted above, platform device 120 may include functionality to allow the user, via the user device 110, to get verified, then initiate a lab test, access information pertaining to their lab test following the lab test, and share their test results (e.g., STD status) with others. Some of these functionalities, at least in part, may be executed using API associated with the instructions instances (e.g., 122a-122e).

Figure 3:
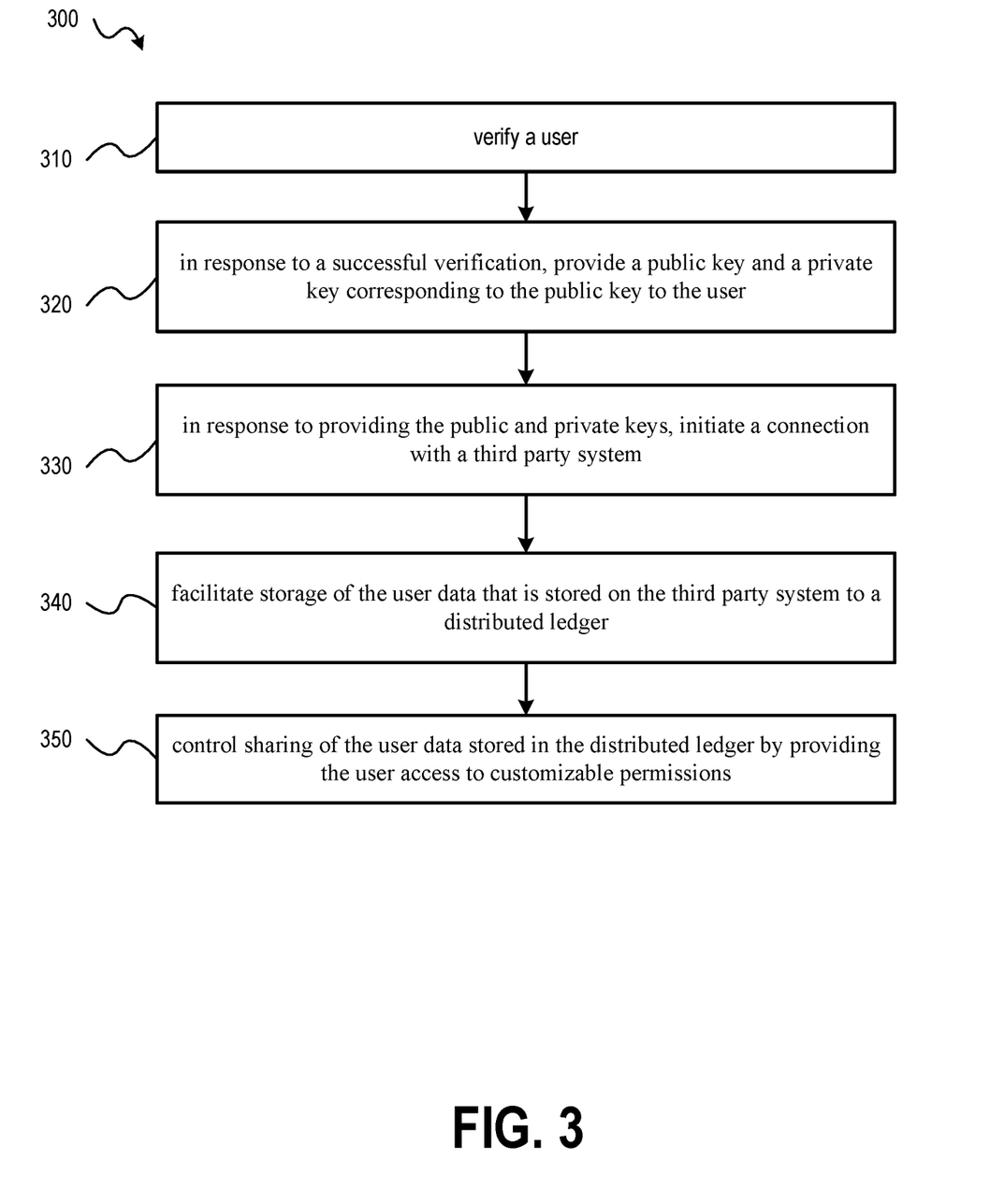
FIG. 3 shows a flow diagram illustrating functionality of a system of FIG. 1 in accordance with aspects of the present disclosure.

FIG. 3 shows a flow diagram illustrating functionality of the system of FIG. 1 in accordance with aspects of the present disclosure. FIG. 3 is now described with respect to the application in which users need to determine with whom they wish to engage, speak, message, or meet and engage in sexual activity. As such, the functionality of the system of FIG. 1 described herein assists the user to securely gather up to date information about their STD status stored at the lab test service provider system; and share, to a dating service provider, details related to their STD status and/or personal details (e.g., dating bio, pictures, STD test results or an indication of whether the user has an STD and/or the latest date on which the user was tested).

As shown in FIG. 3, the method 300 may include, at block 310, verifying a user's real world identity. In embodiments, the user may be verified using an identity verification service provider. As described above, when a user attempts to access the services provided by the platform device 120 (such as the plurality of service described with respect to FIG. 1), the user may first be asked to register at the platform device 120. The registration may include verification of the user. In embodiments, verification may include background checks. These background checks may only allow people who are registered with the government and who they are as claim to be to use the services provided by the platform device 120. As such, verifying a user before letting them access the services reduces the possibility of fraud, identity theft, violence and crime. In aspects, verification includes receiving personal details of the user, for example, name, contact information, and some type of state identification information (e.g., driver's license number, passport number). In aspects, the platform device 120 may also request the user to scan and share pictures of their state identification or passport along with other personal details. The personal details provided by the user during registration may be sent using one or more APIs and instruction instances described above via network 170 to an identity verification service provider. Once the verification is complete, the results are sent back via APIs associated with the identity verification service provider to the platform device 120. If the results are positive, meaning if the user is who he or she claims to be, the user may be allowed to use the service provided by the platform device 120.

The method 300 may then include, at block 320, providing, to the user by the platform device 120, one or more identifications associated with the user's profile on the platform device 120 in response to a successful verification (or registration). As noted above, the one or more identifications may be a personal key and a corresponding private key, and in some embodiments, the user may be issued a platform ID. The platform device 120, in its local memory (e.g., memory 124) may only store the user's platform ID, a copy of the user's public key, and the association between the two. The platform device 120 may not store the private key of the user and any personally information that may identify the user in local memory. In aspects, successful registration may also allow the user to create a dating profile using the platform device 120. The user, therefore, may provide dating related information (e.g., dating bio, dating preferences, social media handle, pictures, etc.). In aspects, the platform device 120 may store the rest of the information provided to the platform device 120 (e.g., information such as name, date of birth, sex, dating profile information, etc., including verification information provided during verification) in a distributed ledger by the platform device 120. In embodiments, the information provided by the user (e.g., dating bio, dating preferences, etc.) may be encrypted using the user's public key before storing (or placing or creating a transactional record) in the distributed ledger. In embodiments, in order to comply with regional data security laws (e.g., GDPR), the platform device 120 may be configured to store an encrypted version of the personal identifiable information (PII) pertaining to the user in an off-chain storage (e.g., in private data collection storage which is separate from the local memory). In such embodiments, the platform device may be configured to store the user's public key and/or public key address into the off-chain storage. In aspects, the platform device 120 may be configured to retrieve and/or identify the information stored in the off-chain storage using the user's public key (or public key address).

The method 300 may then include, at block 330, enabling the user to use the services provided by platform device 120. For example, following being provided the set of keys, the platform device 120 enables the user to initiate a lab test request from a lab service provider (e.g., lab service provider 144), for instance, by initiating a connection with the lab service provider 144. As described above, once the user is verified and is provided a set of keys, the platform device 120 may provide the user the ability to request lab tests, such as by providing a link (e.g., website link) to the lab service provider 144. When the user indicates interest to schedule a lab test, for instance by clicking to the link, the platform device 120 may direct the user to the lab service provider 144, generate a unique ID corresponding to the lab test request, and transmit, via one or more APIs, the unique ID to the lab service provider. The platform device 120 may then associate the unique ID with the user (e.g., by associating the unique ID with the public key or the public key address of the user) in the platform device 120.

The method 300 may then include, at block 340, facilitating storage of a lab result corresponding to the lab test in the distributed ledger, upon completion of the lab test corresponding to the lab test request. For example, following the completion of the lab test, the platform device 120 may enable the lab service provide to map the lab test results to the correct user and store the lab test results directly onto the distributed ledger. To illustrate, when the lab results are ready to be viewed, the platform device 120 may receive a notification, such as in the form of an API call from the API of the lab service provider. As a response to the API call, the platform device 120 may provide the association information between the unique ID and the user, which directs the test results to the blockchain network 172, thereby allowing the test results to be directly stored in the distributed ledger, without the platform device having to ever store the test results in their local memory (e.g., memory 124). As noted above, the lab test results may be encrypted before they are stored in the distributed ledger. The user may be able to view all the information stored in the distributed ledger using the application provided by the platform device 120 and the keys stored within the digital wallet.

The method 300 may then include, at block 350, enabling the user to control distribution of the data stored in the distributed ledger. For example, using smart contracts and by customizing/changing permissions, the user may be able to share one or more details from their personal details (e.g., name, contact information, location, dating bio, dating preferences, STD test results) to the other profiles, for instance which are present on dating service provider's (e.g., dating service provider 142) platform. The shared details may include the day the test was conducted or the day the results were received, results of the test, the type of STD they possess (if any), etc. The user may also have an option to reveal that they have been tested without explicitly revealing whether they have an STD or not. In that scenario, the user's profile may indicate to other users that the user has been tested and may prompt other users to reach out to the person and ask their STD status. In embodiments, the user can not only share information about their STD status on their profile, the users may share their STD test results with other users through smart contracts.

FIG. 3 is now described with respect to the application in which users need to send their COVID-19 status to one or more third parties in order to let the third parties determine whether to allow the user in their facility. The description of FIG. 3 provided in blocks 310 and 320 substantially remain the same, i.e., the platform device 120 may need to verify the user and provide a set of keys to the user. In block 330, instead of enabling the user to request a lab test related to STDs, the platform device 120 may enable the user to take a COVID-19 test. The platform device 120 may enable the user to take a COVID test in a similar fashion as is described above. In embodiments, the platform device 120 may also prompt the user interested to take the COVID-19 test to submit answers to some questions related to their travel info, whether they were around anyone who has tested for COVID, etc. The answer to these questions may be stored in the distributed ledger by the platform device 120. In embodiments, if the user indicates that the user has received a COVID-19 vaccine, the platform device 120 may prompt the user to provide details of the vaccine, for example, the received date, the type of vaccine received, etc. All the information provided related to vaccine may also be stored in the distributed ledger.

Similar to the technique described in block 340, the platform device 120 may facilitate the storage of the COVID-19 test results in the distributed ledger. The user, as described in block 350, may control the distribution of the lab results data stored in the distributed ledger by providing the user access to customizable permissions (e.g., via smart contracts) on the application provided by the platform device 120. To illustrate, using the application provided by platform device 120, the user may customize or change the smart contract permissions/criterions. The selection of criteria/permissions may control the sharing/distribution of their personal information, including COVID-19 status. These criterions/permissions, as noted above, may control the amount of data that is being shared. For example, a user, using smart contracts, may only choose to send a portion of their test result (e.g., just their COVID-19 status in the form of a badge, which may either signify that the user has been tested positive or negative or has recovered after being tested positive, or has received a vaccine. Depending on the status, the badge may assume different color or shape. For example, a green badge or a green "check" sign may signify that the user has taken a test and is free from COVID-19. In other examples, the badge may assume a yellow "check" sign which may signify that the user has contracted the virus but has recovered. In other examples, the badge may assume a red "cross" sign, signifying that the user has tested positive COVID-19. In embodiments, the sharing of COVID-19 related data may trigger a response in the third-party system's (i.e., the system with which the COVID-19 related data is shared). The response may include activating a door that allows the user to enter the third-party system's facility. For example, after getting tested and securing data from the lab service provider to the distributed ledger, the user may attempt to enter the third-party's real world facility. In order to do that, the user may share with the third-party system, using the smart contracts, a green badge indicating that the user is free from COVID-19. Thus, as a result of the sharing of the green badge, the third-party system may activate the door that allows the user to enter the third-party system's facility.

The disclosure above may be applicable to systems used for sharing personal data involving name and surname; social security number; driver's license number and information; employer and employment status; salary; financial records and information; marital status; a home address; an email address such as name.surname@company.com; health records; an identification card number; location data (for example the location data function on a mobile phone); an Internet Protocol (IP) address; a cookie ID; the advertising identifier of a phone; data held by a hospital or doctor, which could be a symbol that uniquely identifies a person; personal details related to smart (e.g., IoT) devices (thermostat settings, payment information, favorite door lock code, favorite safe code, water temperature, Bluetooth, light settings, streaming music and entertainment services, shades, wake words). (The list disclosed above is not exhaustive and non-limiting.) One or more of the above-mentioned personal data may be shared in different environments or settings or service providers.

In one example, the details pertaining to the user could connect to a user's profile controlled, e.g., by the application provided by the platform device, which could further be used in different settings, (e.g., in a hotel room). In such a scenario, the user's preferences for every smart device in the hotel room would be activated by a smart contract upon check-in and deactivated every time a user leaves the room. In such a scenario, the hotel would not have any access to the personal data or user preferences mentioned in this example, nor would these preferences be stored in any hackable, centralized database owned or maintained by the hotel; thus, the user would control and share what they wish, how they wish, with whom and what they wish, and maintain complete control over when they wish to share it. As such, the discussion herein with respect to users accessing, securing, and sharing personal medical data in a dating environment should not be construed as limiting in any way.

The disclosure above describes securing, accessing, and sharing medical data (e.g., STD status). The embodiments of the disclosure are configured such that the system described herein can be configured to comply with various regulatory schemes, such as the Health Insurance Portability and Accountability Act (HIPAA). In examples where other personal data is to be shared, the system may also be configured to comply with regulations relevant to the data to be shared, such as General Data Protection Regulation (GDPR). It will be appreciated that the system may be configured to comply with other regulations that pertain to sharing personal data.

One or ordinary skill in the art would further appreciate that storing data into distributed ledger includes creating a transactional record in the distributed ledger. One or ordinary skill in the art would further appreciate the various illustrative logical blocks, modules, circuits, and algorithm steps described in connection with the disclosure herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present disclosure. Skilled artisans will also readily recognize that the order or combination of components, methods, or interactions that are described herein are merely examples and that the components, methods, or interactions of the various aspects of the present disclosure may be combined or performed in ways other than those illustrated and described herein.

Functional blocks and modules in FIGS. 1-2 may comprise processors, electronics devices, hardware devices, electronics components, logical circuits, memories, software codes, firmware codes, etc., or any combination thereof. Consistent with the foregoing, various illustrative logical blocks, modules, and circuits described in connection with the disclosure herein may be implemented or performed with a general-purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general-purpose processor may be a microprocessor, but in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration.

The functional blocks, and components thereof, of system 100 in embodiments of the present invention may be implemented using processors, electronic devices, hardware devices, electronic components, logical circuits, memories, data storage devices, software codes, firmware codes, etc., or any combination thereof. For example, one or more functional blocks, or some portion thereof, may be implemented as discrete gate or transistor logic, discrete hardware components, or combinations thereof configured to provide logic for performing the functions described herein. Additionally, or alternatively, when implemented in software, one or more of the functional blocks, or some portion thereof, may comprise code segments operable upon a processor to provide logic for preforming the functions described herein.

It is also noted that various components of system 100 are illustrated as single and separate components. However, it will be appreciated that each of the various illustrated components may be implemented as a single component (e.g., a single application, server module, etc.), may be functional components of a single component, or the functionality of these various components may be distributed over multiple devices/components. In such aspects, the functionality of each respective component may be aggregated from the functionality of multiple modules residing in a single, or in multiple devices.

The steps of a method or algorithm described in connection with the disclosure herein may be embodied directly in hardware, in a software module executed by a processor, or in a combination of the two. A software module may reside in RAM memory, flash memory, ROM memory, EPROM memory, EEPROM memory, registers, hard disk, a removable disk, a CD-ROM, cloud based storage or any other form of storage medium known in the art. An exemplary storage medium is coupled to the processor such that the processor can read information from, and write information to, the storage medium. In the alternative, the storage medium may be integral to the processor. The processor and the storage medium may reside in an ASIC. The ASIC may reside in a user terminal, base station, a sensor, or any other communication device. In the alternative, the processor and the storage medium may reside as discrete components in a user terminal.

In one or more exemplary designs, the functions described may be implemented in hardware, software, firmware, or any combination thereof. If implemented in software, the functions may be stored on or transmitted over as one or more instructions or code on a computer-readable medium. Computer-readable media includes both computer storage media and communication media including any medium that facilitates transfer of a computer program from one place to another. Computer-readable storage media may be any available media that can be accessed by a general purpose or special purpose computer. By way of example, and not limitation, such computer-readable media can comprise RAM, ROM, EEPROM, CD-ROM or other optical disk storage, magnetic disk storage or other magnetic storage devices, or any other medium that can be used to carry or store desired program code means in the form of instructions or data structures and that can be accessed by a general-purpose or special-purpose computer, or a general-purpose or special-purpose processor. Also, a connection may be properly termed a computer-readable medium. For example, if the software is transmitted from a website, server, or other remote source using a coaxial cable, fiber optic cable, twisted pair, or digital subscriber line (DSL), then the coaxial cable, fiber optic cable, twisted pair, or DSL, are included in the definition of medium. Disk and disc, as used herein, includes compact disc (CD), laser disc, optical disc, digital versatile disc (DVD), floppy disk and blu-ray disc where disks usually reproduce data magnetically, while discs reproduce data optically with lasers. Combinations of the above should also be included within the scope of computer-readable media.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods, and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

The invention claimed is:

1. A system for controlling sharing of user data, comprising:
a platform device configured to:
access an external identity verification service to verify a real world identity of a user of the platform device;
in response to receipt of a positive verification result from the external identity verification service, generate a public key and a private key corresponding to the public key and store the public key at a local storage of the platform device without storing the private key at the local storage of the platform device, wherein the public key is stored in the local storage to identify the user without storing other user identifiable information at the local storage of the platform device;
transmit the private key to a user device associated with the user;
initiate a connection with a third-party system that stores data pertaining to the user, and wherein initiating the connection with the third-party system further includes:
generating a unique ID corresponding to the connection;
associating the unique ID with the public key of the user; and
transmitting the unique ID to the third-party system;
facilitate storage of the user data that corresponds to the unique ID and that is stored on the third-party system to a distributed ledger, wherein facilitating the storage of the user data stored on the third-party system comprises directing user data stored in the third-party system to the distributed ledger, and wherein the directing includes:
receiving an indication from the third-party system that the user data is available; and
in response to the indication, providing association information between the unique ID and the public key of the user;
control sharing of first data derived from the user data stored in the distributed ledger by providing the user access to customizable permissions; and
share the first data derived from the user data with another third party system for selective performance of a mechanical activity by the another third party system based on the first data;
wherein the user data includes health status test result;
wherein the first data derived from the user data includes an indication of whether the health status result is positive or negative;
wherein in case health status test result is negative, the sharing the first data derived from the user data with the another third-party system results in the selective performance of the mechanical activity based on the first data;
wherein the mechanical activity activates a door that allows the user of the platform device to enter a facility associated with the another third-party system.

2. The system of claim 1, wherein, in response to the successful verification, the platform device is further configured to:
generate a platform ID specific to the user;
provide the user access to the customizable permissions; and
associate the platform ID to the public key of the user.

3. The system of claim 1, wherein the data stored on the third-party system is encrypted prior to storage in the distributed ledger.

4. The system of claim 1, wherein the platform device is further configured to provide a graphical user interface to the user, and wherein the graphical user interface provides functionality for enabling the user to initiate the connection with the third-party system.

5. The system of claim 1, wherein the platform device is configured to facilitate the storage of the data corresponding to the user in the distributed ledger after receiving an indication from the third-party system.

6. The system of claim 5, wherein the indication includes an application programming interface (API) call.

7. The system of claim 1 further comprising a digital wallet corresponding to the user, wherein the digital wallet is configured to store the private key.

8. The system of claim 1, wherein the health status test result is a COVID-19 test result.

9. The system of claim 8, wherein in case the COVID-19 test result is positive, the sharing the first data derived from the user data with the another third-party system results in the selective performance of no mechanical activity based on the first data.

10. The system of claim 8, wherein the third-party system is a non-distributed ledger system, and wherein the another third-party system is a non-distributed ledger system.

11. The system of claim 1, wherein the first data includes non-personally identifiable information related to the user.

12. An apparatus for controlling securing and sharing of user data, the apparatus comprising:
a memory; and
at least one processor coupled to the memory, the at least one processor configured to:
   access an external identity verification service to verify a real world identity of a user of the platform device;
   in response to receipt of a positive verification result from the external identity verification service, generate a public key and a private key corresponding to the public key and store the public key at a local storage of the platform device without storing the private key at the local storage of the platform device, wherein the public key is stored in the local storage to identify the user without storing other user identifiable information at the local storage of the platform device;
   transmit the private key to a user device associated with the user;
   initiate a connection with a third-party system that stores data pertaining to the user, and wherein initiating the connection with the third-party system further includes:
      generating a unique ID corresponding to the connection;
      associating the unique ID with the public key of the user; and
      transmitting the unique ID to the third-party system;
   facilitate storage of the user data that corresponds to the unique ID and that is stored on the third-party system to a distributed ledger, wherein facilitating the storage of the user data stored on the third-party system comprises directing user data stored in the third-party system to the distributed ledger, and wherein the directing includes:
      receiving an indication from the third-party system that the user data is available; and
      in response to the indication, providing association information between the unique ID and the public key of the user;
   control sharing of first data derived from the user data stored in the distributed ledger by providing the user access to customizable permissions; and
   share the first data derived from the user data with another third party system for selective performance of a mechanical activity by the another third party system based on the first data;
wherein the user data includes health status test result;
wherein the first data derived from the user data includes an indication of whether the health status result is positive or negative;
wherein in case health status test result is negative, the sharing the first data derived from the user data with the another third-party system results in the selective performance of the mechanical activity based on the first data;
wherein the mechanical activity includes opening a door that allows the user of the platform device to enter a facility associated with the another third-party system.

13. The apparatus of claim 12, wherein, in response to the successful verification, the at least one processor is further configured to:
generate a platform ID specific to the user;
provide the user access to the customizable permissions; and
associate the platform ID to the public key of the user.

14. The apparatus of claim 12, wherein the data stored on the third-party system is encrypted prior to storage in the distributed ledger.

15. The apparatus of claim 12, wherein the at least one processor is further configured to provide, via a graphical user interface to the user, functionality for enabling the user to initiate the connection with the third-party system.

16. The apparatus of claim 12, wherein the at least one processor is configured to facilitate the storage of the data corresponding to the user in the distributed ledger after receiving an indication from the third-party system.

17. The apparatus of claim 16, wherein the indication includes an application programming interface (API) call.

18. The apparatus of claim 12 further comprising a digital wallet corresponding to the user, wherein the digital wallet is configured to store the private key.

* * * * *